United States Patent [19]

Yamada et al.

[11] 4,373,026

[45] Feb. 8, 1983

[54] MICROBIAL POLYAMIDE OXIDASE PC-3 AND PROCESS FOR PREPARATION THEREOF

[75] Inventors: Hideaki Yamada; Yoshiki Tani; Kimiyasu Isobe, all of Kyoto, Japan

[73] Assignee: Amano Pharmaceutical Co., Ltd., Nagoya, Japan

[21] Appl. No.: 216,302

[22] Filed: Dec. 12, 1980

[30] Foreign Application Priority Data

Dec. 24, 1979 [JP] Japan ................................ 54-166953

[51] Int. Cl.$^3$ .......................... C12R 1/82; C12N 9/06; C12P 21/00
[52] U.S. Cl. .................................... 435/191; 435/935; 435/68
[58] Field of Search ................. 435/68, 189, 191, 935, 435/933, 934, 936, 937

[56] References Cited

PUBLICATIONS

Mann, Further Purification and Properties of the Amine Oxidase of Pea Seedlings, *Biochem. Journal*, vol. 79, 1961, pp. 623–631.
Smith, et al., Further Properties of the Polyamine Oxidase of Barley Leaves, *Phytochemistry*, vol. 13, 1974, pp. 2435–2443.
Razin, et al., The Degradation of Natural Polyamines and Diamines by Bacteria, (1959), *Biochemical Journal*, vol. 71, pp. 551–558.
Tabor, et al., Identification of Flavin Adenine Dinucleotide and Heme in a Homogeneous Spermidine Dehydrogenase from *Serratia Marcescens*, *The Journal of Biological Chemistry*, vol. 20, 1970, pp. 5424–5433.
Hill, Diamine Oxidase, (pea Seedling), Methods in Enzymology, vol. 1713, 1971, pp. 730–735.
Yamada, Monoamine Oxidase, *The Journal of Biological Chemistry*, vol. 237, 1962, pp. 1511–1516.
Hölträ, E. Oxidation of Spermidine and Spermine in Rat Liver, Purification and Properties of Polyamine Oxidase *Biochemistry* vol. 16, 1977, pp. 91–100.

*Primary Examiner*—Thomas G. Wiseman
*Assistant Examiner*—Kathleen S. McGowin
*Attorney, Agent, or Firm*—Browdy and Neimark

[57] ABSTRACT

A novel polyamine oxidase, polyamine oxidase PC-3, takes an important role participating in decomposition and metabolism and polyamines such as spermidine and spermine.

5 Claims, 5 Drawing Figures

MICROBIAL POLYAMIDE OXIDASE PC-3 AND PROCESS FOR PREPARATION THEREOF

FIELD OF THE INVENTION

The present invention relates to novel polyamine oxidase PC-3 derived from a microorganism. Polyamine oxidases are ordinarily enzymes having a catalytic activity for oxidative deamination of polyamines, and in the living body they take an important role participating in decomposition and metabolism of polyamines such as spermidine and spermine.

BACKGROUND OF THE INVENTION

Recently, the interrelation between cancer and an increase of amounts of polyamines in body fluids such as blood, urine and lymph has attracted attention, and the use of a polyamine oxidase as an enzyme for diagnosis of cancers has been developed (see Japanese Patent Application Laid-Open Specification No. 9492/75).

Polyamine oxidases derived from animal and plant tissues as supply sources have heretofore been used. However, each of the polyamine oxidases derived from animal and plant tissues is poor in activity, and it is difficult to obtain them in large quantities. Furthermore, it is very difficult to produce these polyamine oxidases at low costs on an industrial scale.

SUMMARY OF THE INVENTION

As a result of research made with a view of developing a process capable of producing a polyamine oxidase at a low cost on an industrial scale, we found that when *Penicillium chrysogenum* IFO 4626, which is capable of growing with spermidine or spermine as a single carbon-nitrogen source or a single carbon or single nitrogen source, is cultured in a culture medium containing spermidine or spermine, a novel polyamine oxidase PC-3 is produced and accumulated in a large quantity in the culture product. We have now completed the present invention based on this finding.

DETAILED DESCRIPTION OF PREFERRED EMBODIMENTS

Microbial polyamine oxidase PC-3 according to the present invention has the following physicochemical properties.

(1) Reactivity:

As shown by the following reaction formula, the oxidase effects reaction of $H_2O$ and $O_2$ with spermidine to form 1 mol of putrescine, 1 mol of 3-aminopropionaldehyde and 1 mol of hydrogen peroxide from 1 mol of spermidine, and the oxidase effects reaction of $H_2O$ and $O_2$ with spermine to form 1 mol of putrescine, 2 mols of 3-aminopropionaldehyde and 2 mols of hydrogen peroxide.

$$NH_2(CH_2)_3NH(CH_2)_4NH_2 + O_2 + H_2O \longrightarrow$$

spermidine $$NH_2(CH_2)_2CHO + NH_2(CH_2)_4NH_2 + H_2O_2$$

| 3-aminopropion-aldehyde | putrescine | hydrogen peroxide |

$$NH_2(CH_2)_3NH(CH_2)_4NH(CH_2)_3NH_2 + 2O_2 + 2H_2O \longrightarrow$$

spermine $$2NH_2(CH_2)_2CHO + NH_2(CH_2)_4NH_2 + 2H_2O_2$$

| 3-aminopropion-aldehyde | putrescine | hydrogen peroxide |

(2) Substrate Specificity:

As shown in Table 1, the oxidase effects reaction of $O_2$ and $H_2O$ with spermidine and spermine.

TABLE 1

| Substrate (2 mM) | Relative Activity | |
|---|---|---|
|  | pH = 6.5 | pH = 7.5 |
| Methylamine | 0.0 | 0.0 |
| Ethylamine | 0.0 | 0.0 |
| Propylamine | 0.0 | 0.0 |
| Butylamine | 0.0 | 0.0 |
| Phenethylamine | 0.0 | 0.0 |
| Tyramine | 0.0 | 0.0 |
| Dopamine | 0.0 | 0.0 |
| Tryptamine | 0.0 | 0.0 |
| Serotonin | 0.0 | 0.0 |
| Benzylamine | 0.0 | 0.0 |
| Histamine | 0.0 | 0.0 |
| Agmatine | 0.0 | 0.0 |
| Cadaverine | 0.0 | 0.0 |
| Putrescine | 0.0 | 0.0 |
| Spermidine | 10.9 | 0.0 |
| Spermine | 100 | 100 |

Figure 1:
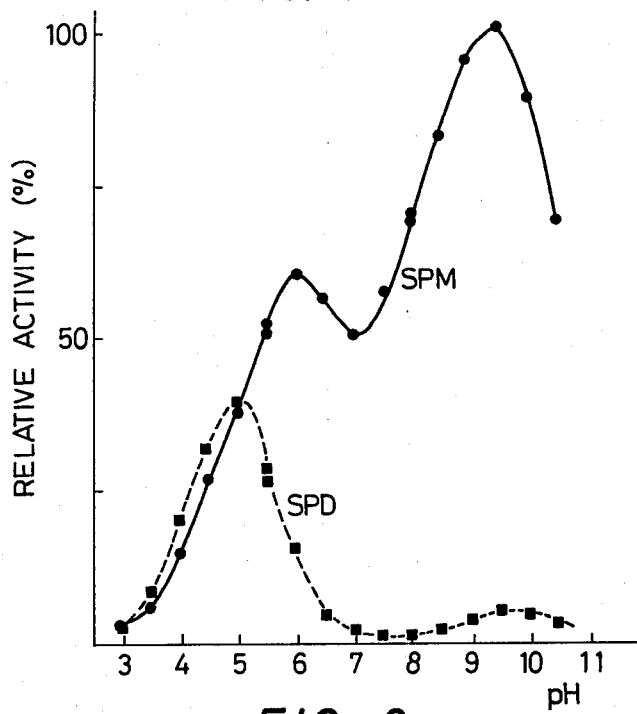
FIG. 1 is a pH activity curve of polyamine oxidase PC-3 of the present invention.

(3) Optimum pH:

The optimum pH for reaction with spermidine is about 5.0 and the optimum pH for reaction with spermine is about 9.5 (see FIG. 1).

Figure 2:
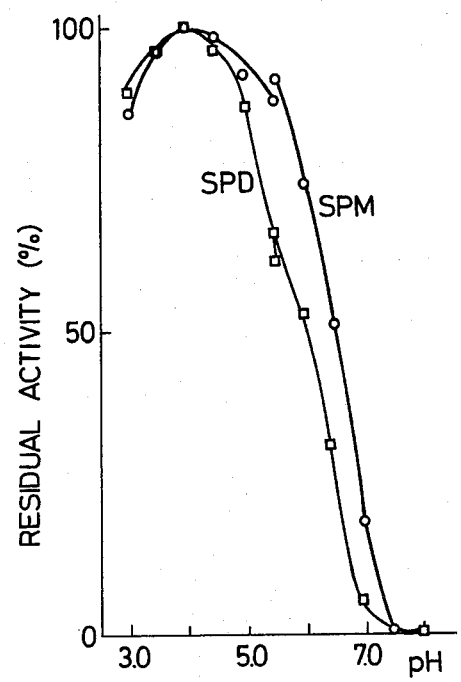
FIGS. 2, 3 and 4 show the pH stability, optimum temperature and temperature stability, respectively.

(4) pH Stability:

In the case where the substrate is either spermidine or spermine, when the oxidase is treated at 30° C. for 10 minutes at pH 3.0 to 5.0, the residual ratio of the activity is higher than 85% (see FIG. 2).

Figure 3:
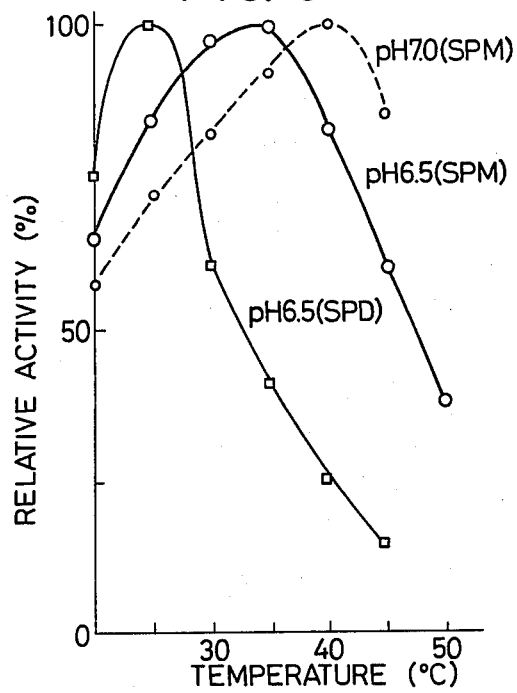

(5) Optimum Temperature:

When spermidine is a substrate, the optimum temperature is about 25° C. at pH 6.5, and when spermine is a substrate, the optimum temperature is about 35° C. at pH 6.5 and is about 40° C. at pH 7.0 (see FIG. 3).

Figure 4:
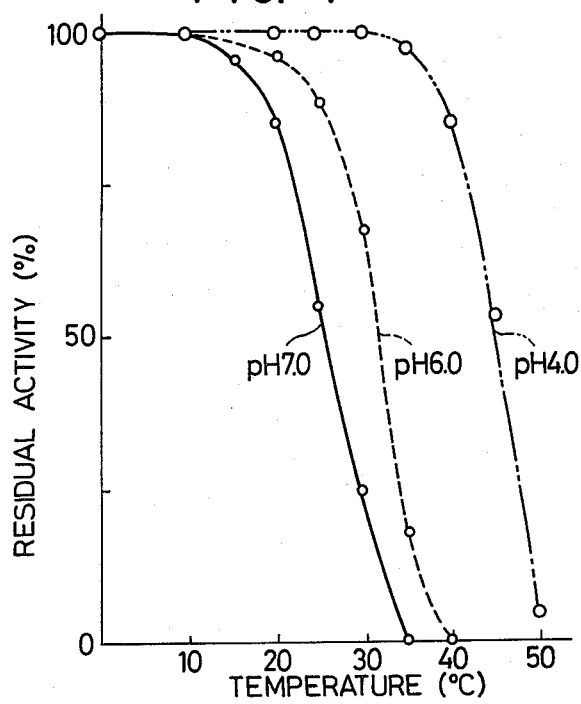

(6) Temperature Stability:

In the case where spermine is a substrate, when the oxidase is treated at 35° C. for 10 minutes at pH 4.0 the residual ratio of the activity is higher than 95%, and when the oxidase is treated at 20° C. for 10 minutes at pH 7.0, the residual ratio of the activity is higher than 85% (see FIG. 4).

Figure 5:
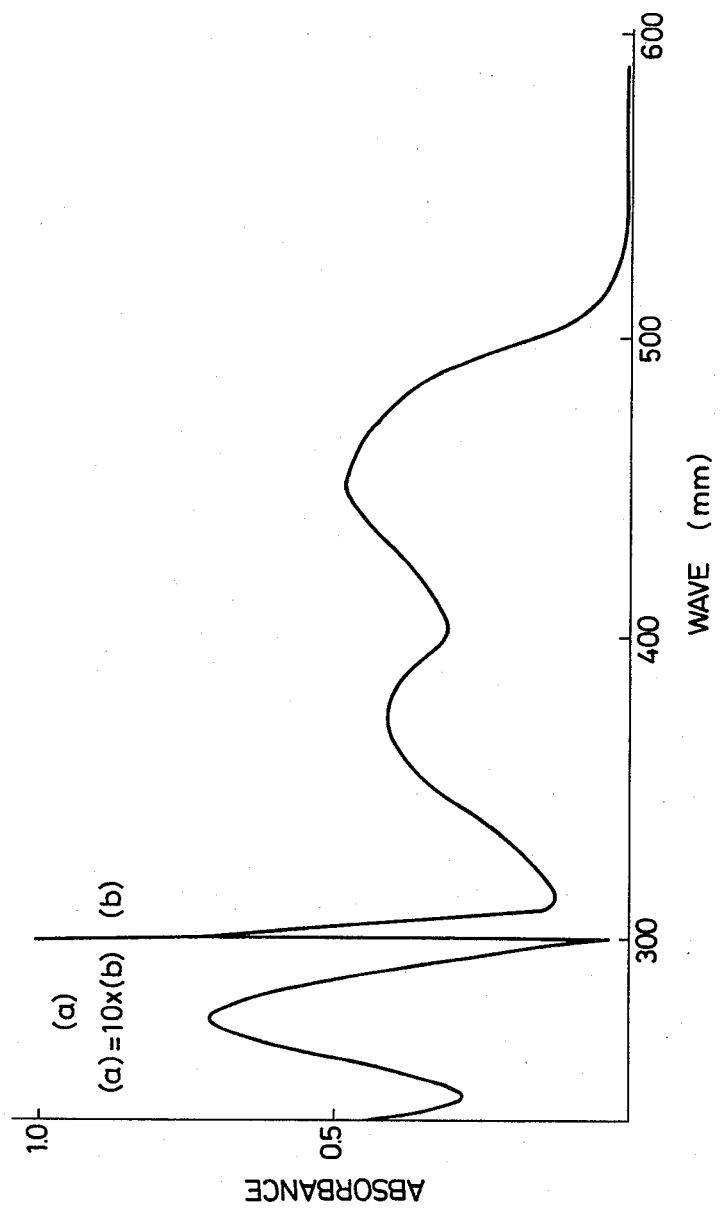
FIG. 5 shows the absorption spectrum.

(7) Absorption Spectrum and Coenzyme:

From the fact that maximum absorptions are observed at 280, 375 and 450 nm in the absorption spectrum, it is confirmed that the oxidase is a flavin protein (see FIG. 5), and FAD is present as a coenzyme in an amount of 2 molecules per molecule of the enzyme.

(8) Influences of Inhibitors and Metal Ions:

(a) Influences of various inhibitors are shown in Table 2 (the concentration of PCMB is 140 μM).

TABLE 2

| Inhibitor (1.4 mM) | Relative Activity (%) SPM | SPD |
| --- | --- | --- |
| Hydroxylamine | 100 | 91.9 |
| Hydrazine | 100 | 100 |
| Phenylhydrazine | 100 | 94.6 |
| Semicarbazide | 100 | 91.9 |
| Isoniazid | 98.6 | 70.3 |
| Iproniazid | 98.6 | 83.4 |
| α,α'-Dipyridyl | 77.7 | 100 |
| 8-Hydroxyquinoline | 91.5 | 100 |
| o-Phenanthroline | 86.2 | 94.6 |
| Sodium azide | 88.3 | 100 |
| EDTA | 95.7 | 95.7 |
| PCMB | 1.1 | 68.4 |
| Monoiodoacetic acid | 9.6 | 65.4 |
| Not added | 100 | 100 |

Note
EDTA: ethylenediamine tetraacetate
PCMB: p-chloromercurybenzoate (b) Influences of metal ions (1.4 mA) are shown in Table 3.

TABLE 3

| Metal Ion | Relative Activity (%) SPM | SPD |
| --- | --- | --- |
| $NH_4^+$ | 95.1 | 100 |
| $Ag^+$ | 2.4 | 0.0 |
| $Li^+$ | 94.1 | 97.2 |
| $Ni^{2+}$ | 45.9 | 85.7 |
| $Cu^{2+}$ | 36.4 | 108.6 |
| $Zn^{2+}$ | 24.4 | 97.1 |
| $Mg^{2+}$ | 80.0 | 65.7 |
| $Hg^{2+}$ | 0.0 | 40.0 |
| $Pb^{2+}$ | 47.6 | 62.9 |
| $Fe^{3+}$ | — | 42.9 |
| $Al^{3+}$ | 91.5 | 0.0 |

In Tables 2 and 3, SPM stands for spermine and SPD stands for spermidine, and the activity is one as measured at pH 9.5 in case of SPM or at pH 5.0 in case of SPD.

(9) Isoelectric Point:

The isoelectric point is 5.4 to 5.6 as measured according to the ampholyte isoelectric point electrophoresis method.

(10) Molecular Weight:

The molecular weight is 160,000 as determined according to the gel filtration method using Sephadex G-200.

(11) Molecular Weight of Subunit:

The molecular weight of the subunit is 80,000.

(12) Crystal Form:

The oxidase takes the form of a needle crystal.

Microbial polyamine oxidase PC-3 having the above-mentioned physicochemical properties is a novel polyamine oxidase which is obviously different from polyamine oxidases derived from animals and plants and other polyamine oxidases derived from microorganisms.

In Table 4, properties of this novel polyamine oxidase is compared with those of polyamine oxidases derived from various origins.

Beef plasma amine oxidase is one disclosed by H. Yamada et al. in The Journal of Biological Chemistry, 237, pages 1511 to 1516 (1962), and rat liver polyamine oxidase is one disclosed by E. Hölttä in Biochemistry, 16, pages 91 to 100 (1977). Pea polyamine oxidase is one disclosed by P. J. G. Mann in Biochemical Journal, 79, pages 623 to 631 (1961) and Method in Enzymology, 17B, pages 730 to 735, and barley polyamine oxidase is one disclosed by P. A. Smith in Phytochemistry, 13, pages 2437 to 2443 (1974) and ibid, 11, pages 899 to 910 (1972). *Serratia marcescens* spermidine dehydrogenase is one disclosed by C. W. Tabor et al. in The Journal of Biological Chemistry, 245, pages 5424 to 5433 (1970) and *Pseudomonas aeruginosa* polyamine oxidase is one disclosed by S. Razin et al. in Biochemical Journal, 71, pages 551 to 558 (1959).

TABLE 4

| | Polyamine oxidase PC-3 of Present Invention | Beef plasma amine Oxidase | Rat Liver Polyamine Oxidase | Pea Polyamine Oxidase |
| --- | --- | --- | --- | --- |
| Substrate Specificity | reacting only with spermidine and spermine | reacting with spermidine, spermine and other monamine | reacting with spermidine and spermine | strongly reacting with cadaverine and putrescine and reacting with spermidine |
| Decomposition Product of $NH_2(CH_2)_3-NH(CH_2)_4NH_2$(spermidine) | $NH_2(CH_2)_2CHO$, $NH_2(CH_2)_4NH_2, H_2O_2$ | $OHC(CH_2)_2NH-(CH_2)_4NH_2$, $NH_3, H_2O_2$ | $NH_2(CH_2)_2CHO$, $NH_2(CH_2)_4NH_2$, $H_2O_2$ | $NH_2(CH_2)_3NH-(CH_2)_3CHO$, $H_2O_2, NH_3$ |
| Decomposition Product of $NH_2(CH_2)_3-NH(CH_2)_4NH(CH_2)_3NH_2$ (spermine) | $NH_2(CH_2)_2CHO$, $NH_2(CH_2)_4NH_2, H_2O_2$ | $OHC(CH_2)_2NH-(CH_2)_4NH(CH_2)_2-CHO, NH_3, H_2O_2$ | $NH_2(CH_2)_2CHO$, $NH_2(CH_2)_4NH_2$, $H_2O_2$ | |
| Inhibitor | not inhibited by carbonyl reagent | | inhibited by carbonyl reagent | inhibited by carbonyl reagent, chelate compound and $Cu^{2+}$ |
| Optimum pH | 5.0 (to spermidine), 9.5 (to spermine) | 7.2 | about 10 | 7.0 (to putrescine) |
| Molecular Weight | 160,000 | 240,000 | 55,000–61,000 | 96,000 |
| Isoelectric Point | 5.4–5.6 | | 4.9 | |
| Coenzyme, etc. | 2 molecules of FAD in one molecule | $Cu^{2+}$ contained | less than 1 molecule of FAD in one molecule | $Cu^{2+}$ |

| | Barley Polyamine Oxidase | Serratia Spermidine dehydrogenase | Pseudomonas Polyamine Oxidase |
| --- | --- | --- | --- |
| Substrate | strongly react- | strongly | reacting with spermidine, |

TABLE 4-continued

| Specificity | ing with spermine and reacting with spermidine | reacting with putrescine and spermidine and reacting with spermine | spermine, cadaverine, putrescine and agmatine |
|---|---|---|---|
| Decomposition Product of $NH_2(CH_2)_3$—$NH(CH_2)_4NH_2$(spermidine) | $NH_2(CH_2)_3CHO$, $NH_2(CH_2)_3NH_2$, $H_2O_2$ | $NH_2(CH_2)_3CHO$, $NH_2(CH_2)_3NH_2$ | $NH_2(CH_2)_3NH_2$, $NH_2(CH_2)_3CHO$ |
| Decomposition Product of $NH_2(CH_2)_3$—$NH(CH_2)_4NH(CH_2)_3NH_2$ (spermine) | $NH_2(CH_2)_3NH(CH_2)_3$—$CHO$, $NH_2(CH_2)_3NH_2$, $H_2O_2$ | $NH_2(CH_2)_3NH$—$(CH_2)_3CHO$, $NH_2(CH_2)_3NH_2$ | $NH_2(CH_2)_3NH(CH_2)_4NH_2$, $NH_2(CH_2)_2CHO$ |
| Inhibitor | | | |
| Optimum pH | 6.5 (spermidine), 4.5 (spermine) | 6.5 | 7.0–7.2 |
| Molecular Weight | | 76,000 | |
| Isoelectric Point | | | |
| Coenzyme, etc. | FAD | FAD | |

As will be apparent from Table 4, none of polyamine oxidases derived from animals, plants and microorganisms are in agreement with polyamine oxidase PC-3 of the present invention in all of the substrate specificity, the mode of decomposition of spermidine and spermine, the behaviors to inhibitors, the optimum pH, the molecular weight and the isoelectric point.

Novel polyamine oxidase PC-3 is obtained by culturing *Penicillium chrysogenum* IFO 4626. Any of synthetic and natural culture media containing appropriate amounts of carbon sources, nitrogen sources, inorganic substances and other nutrients may be used. Either liquid media or solid media may be used, but a liquid medium is oridinarily used. At least one polyamine oxidase PC-3 inducer such as spermidine or spermine is appropriately incorporated in such culture medium.

The cultivation conditions will now be described. The pH at the start of culturing is ordinarily 4.0 to 7.0 and preferably about 5.0 to about 6.0. The culturing temperature is ordinarily 20° to 40° C. and preferably 25° to 35° C. If cultivation is conducted under these conditions for 12 to 120 hours, polyamine oxidase PC-3 is formed and accumulated in a large amount in the culture product.

Polyamine oxidase PC-3 thus formed and accumulated in the culture product is collected according to the following procedures. Since polyamine oxidase PC-3 is present mainly in cells, after completion of cultivation the cells are collected by filtration or the like, washed with water or a buffer solution and suspended in an appropriate buffer solution having a pH value of 5.0 to 8.0 to extract polyamine oxidase PC-3 contained in the cells.

In order to further purify crude polyamine oxidase PC-3 obtained from the cell extract, the pH value of the extract is adjusted to 2.5 to 4.5 by addition of an acid or dialysis to precipitate polyamine oxidase PC-3. The operation of solubilizing the precipitate at a salt concentration corresponding to a level of 1 to 40% of the saturation concentration of ammonium sulfate and the operation of dialyzing the solubilized precipitate solution by an acidic buffer solution having a pH of 2.5 to 4.5 to form a precipitate of polyamine oxidase PC-3 are repeated. By this treatment, the specific activity is increased to a level about 100 times the original activity. The enzyme solution formed by solubilizing the precipitate is then passed through a Sephadex G-200 column, and the recovered active fraction is passed through DEAE-cellulose equilibrated with a buffer solution having a pH of 3.0 to 4.0 and then passed through DEAE-cellulose equilibrated with a buffer solution having a pH of 4.0 to 6.0. The recovered active fraction is passed through a Sephadex G-200 column again. Polyamine oxidase PC-3 which has been purified to show a single spot at the disc electrophoresis is crystallized by ammonium sulfate. The specific activities and recovery ratios at the steps in the purifing procedure from the cell extract to the passage through the Sephadex G-200 column are shown in Table 5.

TABLE 5

| | Capacity (ml) | SPM-act* (pH = 6.5) | Protein** (280 nm) | Specific Activity (U/mg) | Recovery Ratio (%) |
|---|---|---|---|---|---|
| Cell extract | 8200 | 33.8 277160 | 34.4 282080 | 1.0 | 100 |
| Ammonium sulfate solubilization-1 | 1540 | 170 261800 | 9.66 14877 | 17.6 | 94.5 |
| Ammonium sulfate solubilization-2 | 106 | 1931 204730 | 20.65 2189 | 93.5 | 78.2 |
| First Sephadex G-200 | 160 | 932 149120 | 1.45 232 | 642 | 53.8 |
| First DEAE-cellulose | 200 | 743 148600 | 0.597 119.4 | 1245 | 53.6 |
| Second DEAE-cellulose | 65 | 1502 97650 | 0.610 39.7 | 2460 | 35.7 |
| Second Sephadex G-200 | 71 | 1366 97000 | 0.555 39.4 | 2460 | 35.0 |

Note
*the upper value shows the unit activity (U/ml) and the lower value shows the total activity in case of spermine as the substrate.
**the upper value shows the unit amount mg/ml and the lower value shows the total amount (mg).

The method used in the present invention for determining the activity of polyamine oxidase PC-3 will now be described.

In 100 ml of a 0.1 M potassium phosphate buffer solution (pH 6.5) are dissolved 10 mg of 4-aminoantipyrine, 0.2 ml of phenol and 10 mg of peroxidase, and 0.5 ml of spermine (10 mM) or spermidine (10 mM) and 0.5 ml of the enzyme solution are added to 1.5 ml of the so formed coloring reagent and reaction is carried out at 35° C. The quantity of the change of the absorbance at 505 nm per minute is measured. The polyamine oxidase activity units of the enzyme solution are calculated in the following manner. The amount of the polyamine oxidase forming 1.0 μM of hydrogen peroxide per minute is defined as 1 unit. This one unit of the polyamine oxidase corresponds to increase of 0.008 of the absorbance at 505 nm per minute.

The new procedures to determine putrescine, spermidine and spermine were firstly established by the end point assay method using polyamine oxidase PC-3 and putrescine oxidase.

Method 1: Spermidine and spermine were first oxidized with polyamine oxidase (step A). To the reaction mixture, putrescine oxidase was added to oxidize putrescine (step B). Putrescine and spermidine in another reaction mixture were oxidized with putrescine oxidase (step C).

Method 2: Putrescine and spermidine were first oxidized with putrescine oxidase (step A). To the reaction mixture, polyamine oxidase was added to oxidize spermine (step B). Spermidine and spermine in another reaction mixture were oxidized with polyamine oxidase (step C). The amounts of putrescine, spermidine and spermine were determined from the absorbance values at each step A, B and C.

The present invention will now be described with reference to the following example.

EXAMPLE 1

*Penicillium chrysogenum* IFO 4626 was inoculated on 30 l of a culture medium comprising 0.1% of $NaNO_3$, 0.1% of $KH_2PO_4$, 0.05% of $MgSO_4.7H_2O$, 0.05% of KCl and 3.0% of glucose (the pH value before sterilization was 5.5) and cultivation was conducted at 28° C. for 48 hours. The so obtained seed culture liquid was added to 220 l of a culture medium comprising 0.1% of glucose, 0.02% of $MgSO_4.7H_2O$, 0.15% of $K_2HPO_4$, 0.1% of $KH_2PO_4$ and 0.025% of spermidine (the pH before sterilization was 5.5), and culturing was conducted at 28° C. for 48 hours. The culture medium was filtered to obtain about 1.7 Kg of cells. The cells were washed several times with a 0.01 M potassium phosphate buffer solution (pH 6.0), suspended in about 6 l of the same buffer solution and disrupted by a Dyno mill. The obtained extract was subjected to centrifugal separation at 7000 rpm for 20 minutes to separate the cell residue and obtain 8200 ml of the supernatant. The enzymatic activity of the supernatant was 33.8 U/ml. The pH value of the supernatant was adjusted to 3.8 by acetic acid and the formed precipitate was separated from the supernatant by centrifugal separation at 7000 rpm for 20 minutes. Polyamine oxidase PC-3 contained in the precipitate was solubilized by suspending the precipitate in a 0.01 M acetate buffer solution and adding ammonium sulfate so that the concentration corresponded to 10% of the saturation concentration. The isoluble fraction was removed by centrifugal separation at 7000 rpm for 20 minutes to obtain 1540 ml of the supernatant. The enzyme in the supernatant was transferred to the precipitate fraction by dialysis with a 0.01 M acetate buffer solution (pH 3.8). The enzyme in the precipitate fraction was collected by the same centrifugal separation as described above and dissolved in 106 ml of a 0.01 M acetate buffer solution containing ammonium sulfate at a concentration corresponding to 10% of the saturation concentration. The solubilized polyamine oxidase was precipitated by increasing the ammonium sulfate concentration to 90% of the saturation concentration and was then condensed (10 ml) was passed through a Sephadex G-200 column equilibrated with a 0.01 M acetate buffer solution containing ammonium sulfate at a concentration corresponding to 10% of the saturation concentration. The obtained active fraction (160 ml) was passed through a column of DEAE-cellulose (100 ml) equilibrated with a 0.01 M acetate buffer solution (pH 3.8) and dialyzed by a 0.01 M acetate buffer solution (pH 3.8). The dialyzed enzyme solution was passed again through a DEAE-cellulose column (the volume was 20 ml) equilibrated with a 0.01 M acetate buffer solution, and the enzyme solution was concentrated and passed through a Sephadex G-200 column (the volume was 300 ml) equilibrated with a 0.01 M acetate buffer solution. The obtained active fraction was concentrated and ammonium sulfate was added to effect crystallization. Polyamine oxidase PC-3 was obtained in the form of a needle crystal in a yield of 35%.

Differential determination of putrescine, spermidine and spermine by using polyamine oxidase PC-3 will be shown.

Method 1: In the presence of putrescine, spermidine and spermine, spermidine and spermine are first oxidized with polyamine oxidase PC-3 at pH 5.0. After completion of the reaction, its pH was adjusted to around 8.5 and the absorbance value (by 505 nm) is measured (step A). At step A, putrescine is not oxidized. Spermidine and spermine are completely oxidized to putrescine according to Scheme.

The absorbance change at step A shows the molar concentrations of spermidine plus twice of spermine. Putrescine oxidase is then added to the reaction mixture at step A, and the reaction is continued until putrescine is completely oxidized (step B). At step B, total putrescine, which consists of firstly presented one and that produced by polyamine oxidations at step A, are oxidized. Therefore, the absorbance change at step B shows the total concentrations of putrescine plus spermidine plus spermine. Where as the absorbance value, which is measured at the end of step B, shows the absorbance change at step A plus that at step B, the absorbance change at step B is obtained by subtracting the absorbance value at step A from that at step B. When another reaction mixture containing putrescine, spermidine and spermine is also oxidized with putrescine oxidase at pH 8.5, putrescine and spermidine are completely oxidized (step C). The absorbance change at step C shows the concentrations of putrescine plus spermidine. From these results, the absorbance changes at steps A, B and C ($Y_a$, $Y_b$, $Y_c$) were defined by eqs. 1, 2 and 3, respectively.

$$Y_a = [SPD] + 2[SPM] \quad (1)$$

$$Y_b = [PUT] + [SPD] + [SPM] \quad (2)$$

$$Y_c = [PUT] + [SPD] \quad (3)$$

Where, [PUT], [SPD] and [SPM] represent the concentrations of putrescine, spermidine and spermine, respectively. Therefore, the concentrations or the amounts of putrescine, spermidine and spermine could be calculated as follows.

$$[PUT] = 2Y_b - Y_a - Y_c \quad (4)$$

$$[SPD] = Y_a + 2Y_c - 2Y_b \quad (5)$$

$$[SPM] = Y_b - Y_c \quad (6)$$

Method 2: In the presence of putrescine, spermidine and spermine, putrescine and spermidine are first oxidized with putrescine oxidase at pH 8.5. After completion of the reaction, its pH was adjusted to around 5.0 and the absorbance value (by 505 nm) is measured (step A). Step A is identical to step C of Method 1, in which the absorbance change shows the concentrations of putrescine plus spermidine. Polyamine oxidase PC-3 is then added to the reaction mixture at step A, and the reaction is continued until spermine is completely oxidized (step B). The absorbance change at step B shows twice of molar concentration of spermine. Where as the absorbance value, which was measured at the end of step B, shows the adsorbance change at step A plus that at step B, the absorbance change at step B was obtained by subtracting the absorbance value at step A from that at step B. When another reaction mixture containing putrescine, spermidine and spermine is oxidized with polyamine oxidase PC-3 at pH 5.0, spermidine and spermine are completely oxidized without oxidation of putrescine just as step A of Method 1. The absorbance change at step C shows the molar concentrations of spermidine plus twice of spermine. From these results, the absorbance changes at steps A, B and C ($Y_a$, $Y_b$, $Y_c$) are defined by eqs. 7, 8 and 9, respectively.

$$Y_a = [PUT] + [SPD] \quad (7)$$

$$Y_b = 2[SPM] \quad (8)$$

$$Y_c = [SPD] + 2[SPM] \quad (9)$$

Therefore, the concentrations or the amounts of putrescine, spermidine and spermine could be calculated by eqs. 10, 11 and 12.

$$[PUT] = Y_a + Y_b - Y_c \quad (10)$$

$$[SPD] = Y_c - Y_b \quad (11)$$

$$[SPM] = \tfrac{1}{2} Y_b \quad (12)$$

What is claimed is:

1. Microbial polyamine oxidase PC-3 having the following physicochemical properties:
(1) Reactivity:
   it reacts with spermidine to form 1 mol of putrescine, 1 mol of 3-aminopropionaldehyde and 1 mol of hydrogen peroxide from 1 mol of spermidine and it reacts with spermine to form 1 mol of putrescine, 2 mol of 3-aminopropionaldehyde and 2 mols of hydrogen peroxide from 1 mol of spermine;
(2) Substrate specificity:
   it reacts with spermidine and spermine, but it does not react with other amines;
(3) Optimum pH value:
   the optimum pH for reaction with spermidine is about 5.0 and the optimum pH for reaction with spermine is about 9.5;
(4) pH Stability:
   when it is treated at 30° C. for 10 minutes, the residual ratio of the activity with either spermidine or spermine as the substrate at a pH from 3.0 to 5.0 is higher than 85%;
(5) Optimum temperature:
   when spermidine is a substrate, the optimum temperature is about 25° C. at a pH of 6.5 and when spermine is a substrate, the optimum temperature is about 35° C. at a pH of 6.5 and is about 40° C. at a pH of 7.0;
(6) Temperature stability:
   in the case where spermine is a substrate, when it is treated at 35° C. for 10 minutes at a pH of 4.0, the residual ratio of the activity is higher than 95%, and if it is treated at 20° C. for 10 minutes at a pH of 7.0, the residual ratio of the activity is higher than 85%;
(7) Absorption spectrum and coenzyme:
   from the fact that maximum absorptions are observed at 375 nm and 450 nm in the absorption spectrum, it is confirmed that the oxidase is a flavin protein, and FAD is present as a coenzyme in an amount of 2 molecules per molecule of the oxidase;
(8) Influences of inhibitors and metal ions:
   in the case where spermine is a substrate, the activity is inhibited by PCMB, monoiodoacetic acid, a silver ion and a mercury ion, and in the case where spermidine is a substrate, the activity is inhibited by a silver ion and an aluminum ion;
(9) Isoelectric point:
   the isoelectric point is 5.4 to 5.6;
(10) Molecular weight:
   the molecular weight is 160,000 as determined according to the gel filtration method using Sephadex G-200;
(11) Molecular weight of Subunit:
   the molecular weight of the subunit is 80,000 as determined according to the SDS disc electrophoresis method; and
(12) Crystal form:
   it takes the form of a needle crystal.

2. A process for the preparation of microbial polyamine oxidase having the following physicochemical properties:
(1) Reactivity:
   it reacts with spermidine to form 1 mol of putrescine, 1 mol of 3-aminopropionaldehyde and 1 mol of hydrogen peroxide from 1 mol of spermidine and it reacts with spermine to form 1 mol of putrescine, 2 mol of 30 aminopropionaldehyde and 2 mols of hydrogen peroxide from 1 mol of spermine;
(2) Substrate specificity:
   it reacts with spermidine and spermine, but it does not react with other amines;
(3) Optimum pH value:
   the optimum pH for reaction with spermidine is about 5.0 and the optimum pH for reaction with spermine is about 9.5;
(4) pH Stability:
   when it is treated at 30° C. for 10 minutes, the residual ratio of the activity with either spermidine or spermine as the substrate at a pH from 3.0 to 5.0 is higher than 85%;
(5) Optimum temperature:

when spermidine is a substrate, the optimum temperature is about 25° C. at a pH of 6.5 and when spermine is a substrate, the optimum temperature is about 35° C. at a pH of 6.5 and is about 40° C. at a pH of 7.0;

(6) Temperature stability:
in the case where spermine is a substrate, when it is treated at 35° C. for 10 minutes at a pH of 4.0, the residual ratio of the activity is higher than 95%, and if it is treated at 20° C. for 10 minutes at a pH of 7.0, the residual ratio of the activity is higher than 85%;

(7) Absorption spectrum and coenzyme:
from the fact that maximum absorptions are observed at 375 nm and 450 nm in the absorption spectrum, it is confirmed that the oxidase is a flavin protein, and FAD is present as a coenzyme in an amount of 2 molecules per molecule of the oxidase;

(8) Influence of inhibitors and metal ions:
in the case where spermine is a substrate, the activity is inhibited by PCMB, monoiodoacetic acid, a silver ion and a mercury ion, and in the case where spermidine is a substrate, the activity is inhibited by a silver ion and aluminum ion;

(9) Isoelectric point:
the isoelectric point is 5.4 to 5.6;

(10) Molecular weight:
the molecular weight is 160,000 as determined according to the gel filtration method using Sephadex G-200;

(11) Molecular weight of Subunit:
the molecular weight of the subunit is 80,000 as determined according to the SDS disc electrophoresis method; and

(12) Crystal form:
it takes the form of a needle crystal, which comprises, culturing a strain of the genus penicillium producing said oxidase in a nutrient culture medium containing spermidine or spermine under conditions sufficient to accumulate said oxidase and recovering the oxidase.

3. A process for the preparation of microbial polyamine oxidase PC-3 according to claim 2, wherein culture cells are suspended in a buffer solution having a pH value of 5.0 to 8.0 to extract polyamine oxidase PC-3 contained in the cells, adjusting the pH of the extract to 2.5 to 4.5 to precipitate polyamine oxidase PC-3, solubilizing the precipitate by adjusting the salt concentration corresponding to a level of 1 to 40% of the saturation concentration of ammonium sulfate, precipitating polyamine oxidase PC-3 by dialysis of the solubilized precipitate solution with an acidic buffer solution having a pH of 2.5 to 4.5 and a concentration lower than 0.05 M, and repeating said solubilizing and precipitating operations.

4. A process for the preparation of microbial polyamine oxidase PC-3 according to claim 2, wherein polyamine oxidase PC-3 obtained according to the process set forth in claim 3 is passed through Sephadex G-200 and is then passed through DEAE-cellulose having the pH adjusted to 3.0 to 4.0, the obtained active fraction is passed through DEAE-cellulose having the pH adjusted to 4.0 to 6.0 and is then passed through a Sephadex G-200 column to obtain an active fraction, and the active fraction is crystallized by ammonium sulfate.

5. A process according to claim 2, 3 or 4, wherein said strain of the genus Penicillium is *Penicillium chyrosogenum* IFO 4626.

* * * * *